US007132244B2

(12) United States Patent
Jackowski et al.

(10) Patent No.: US 7,132,244 B2
(45) Date of Patent: Nov. 7, 2006

(54) BETAINE/GABA TRANSPORT PROTEIN BIOPOLYMER MARKER INDICATIVE OF INSULIN RESISTANCE

(75) Inventors: George Jackowski, Kettleby (CA); John Marshall, Toronto (CA)

(73) Assignee: Syn X Pharma, Inc., Ontario (CA)

( * ) Notice: Subject to any disclaimer, the term of this patent is extended or adjusted under 35 U.S.C. 154(b) by 0 days.

(21) Appl. No.: 09/992,067

(22) Filed: Nov. 21, 2001

(65) Prior Publication Data

US 2003/0096431 A1    May 22, 2003

(51) Int. Cl.
*G01N 33/53* (2006.01)
(52) U.S. Cl. ............... 435/7.1; 435/7.2; 435/7.21; 436/63; 436/86; 436/173; 436/518; 530/350
(58) Field of Classification Search .............. 435/7.1, 435/7.2, 7.92, 7.94, 810; 436/514, 536, 86, 436/63, 151
See application file for complete search history.

(56) References Cited

U.S. PATENT DOCUMENTS

| 5,062,935 | A |   | 11/1991 | Schlag et al. |   |
|---|---|---|---|---|---|
| 5,766,848 | A |   | 6/1998 | Borden |   |
| 6,020,208 | A |   | 2/2000 | Hutchens et al. |   |
| 6,225,047 | B1 | * | 5/2001 | Hutchens et al. | 435/7.1 |
| 2002/0164668 | A1 | * | 11/2002 | Durham et al. | 435/7.92 |

FOREIGN PATENT DOCUMENTS

| WO | WO 90/14148 | 11/1990 |
|---|---|---|
| WO | WO 93/24834 | 12/1993 |
| WO | WO 98/07036 | 2/1998 |
| WO | WO 01/63280 | 8/2001 |
| WO | WO 01/75454 | 10/2001 |

OTHER PUBLICATIONS

Zhang et al. Neurobiology of Aging, vol. 26, p. 207 (2005).*
Takahashi et al., "Rapid and Sensitive Immunoassay for the Measurement of Serum S100β Using Isoform-specific Monoclonal Antibody", Clinical Chemistry 45, No. 8, (1999) pp. 1307-1311.
Richter et al., "Composition of the peptide fraction in human blood plasma: database of circulating human peptides", Journal of Chromatography B; 726 (1999) pp. 25-35.
Bristow, et al., "Specific Activity of $\alpha_1$ Proteinase Inhibitor and $\alpha_2$ Macroglobulin in Human Serum: Application to Insulin-Dependent Diabetes Mellitus", Clinical Immunology & Immunopathology (1998) vol. 89, No. 3, pp. 247-259.
Trefz, et al., "Establishment of an Enzyme-Linked Immuno-Sorbent Assay for Urinary Trypsin Inhibitor by Using a Monoclonal Antibody", Journal of Immunoassay (1991), vol. 12, No. 3, pp. 347-369.
M. Hua et al, "Transgenic Mice Overexpressing -aminobutyric Acid Transporter Subtype I Develop Obesity", Cell Research, 10(4):303-310 (Dec., 2000).

* cited by examiner

*Primary Examiner*—Long V. Le
*Assistant Examiner*—Jacob Cheu
(74) *Attorney, Agent, or Firm*—McHale & Slavin, P.A.

(57) ABSTRACT

The instant invention involves the use of a combination of preparatory steps in conjunction with mass spectroscopy and time-of-flight detection procedures to maximize the diversity of biopolymers which are verifiable within a particular sample. The cohort of biopolymers verified within such a sample is then viewed with reference to their ability to evidence at least one particular disease state; thereby enabling a diagnostician to gain the ability to characterize either the presence or absence of at least one disease state relative to recognition of the presence and/or the absence of the biopolymer, predict disease risk assessment, and develop therapeutic avenues against the disease.

9 Claims, 3 Drawing Sheets
(3 of 3 Drawing Sheet(s) Filed in Color)

BETAINE/GABA TRANSPORT PROTEIN BIOPOLYMER MARKER INDICATIVE OF INSULIN RESISTANCE

FIELD OF THE INVENTION

This invention relates to the field of characterizing the existence of a disease state; particularly to the utilization of mass spectrometry to elucidate particular biopolymer markers indicative or predictive of a particular disease state, and most particularly to specific biopolymer markers whose up-regulation, down-regulation, or relative presence in disease vs. normal states has been determined to be useful in disease state assessment and therapeutic target recognition, development and validation.

BACKGROUND OF THE INVENTION

Methods utilizing mass spectrometry for the analysis of a target polypeptide have been taught wherein the polypeptide is first solubilized in an appropriate solution or reagent system. The type of solution or reagent system, e.g., comprising an organic or inorganic solvent, will depend on the properties of the polypeptide and the type of mass spectrometry performed and are well-known in the art (see, e.g. Vorm et al. (1994) Anal. Chem. 66:3281 (for MALDI) and Valaskovic et al. (1995) Anal. Chem. 67:3802 (for ESI)). Mass spectrometry of peptides is further disclosed, e.g. in WO 93/24834 by Chait et al.

In one prior art embodiment, the solvent is chosen so that the risk that the molecules may be decomposed by the energy introduced for the vaporization process is considerably reduced, or even fully excluded. This can be achieved by embedding the sample in a matrix, which can be an organic compound, e.g., sugar, in particular pentose or hexose, but also polysaccharides such as cellulose. These compounds are decomposed thermolytically into $CO_2$ and $H_2O$ so that no residues are formed which might lead to chemical reactions. The matrix can also be an inorganic compound, e.g., nitrate of ammonium which is decomposed practically without leaving any residues. Use of these and other solvents are further disclosed in U.S. Pat. No. 5,062,935 by Schlag et al.

Prior art mass spectrometer formats for use in analyzing the translation products include ionization (I) techniques, including but not limited to matrix assisted laser desorption (MALDI), continuous or pulsed electrospray (ESI) and related methods (e.g., IONSPRAY or THERMOSPRAY), or massive cluster impact (MCI); these ion sources can be matched with detection formats including linear or non-linear reflection time-of-flight (TOF), single or multiple quadropole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of protein have been detected, for example, using ESI (Valaskovic, G. A. et al., (1996) Science 273:1199–1202) or MALDI (Li, L. et al., (1996) J. Am. Chem. Soc. 118:1662–1663) mass spectrometry.

ES mass spectrometry has been introduced by Fenn et al. (J. Phys. Chem. 88, 4451–59 (1984); PCT Application No. WO 90/14148) and current applications are summarized in recent review articles (R. D. Smith et al., Anal. Chem. 62, 882–89 (1990) and B. Ardrey, Electrospray Mass Spectrometry, *Spectroscopy Europe,* 4, 10–18 (1992)). MALDI-TOF mass spectrometry has been introduced by Hillenkamp et al. ("Matrix Assisted UV-Laser Desorption/Ionization: A New Approach to Mass Spectrometry of Large Biomolecules," Biological Mass Spectrometry (Burlingame and McCloskey, editors), Elsevier Science Publishers, Amsterdam, pp. 49–60, 1990). With ESI, the determination of molecular weights in femtomole amounts of sample is very accurate due to the presence of multiple ion peaks which all could be used for the mass calculation.

The mass of the target polypeptide determined by mass spectrometry is then compared to the mass of a reference polypeptide of known identity. In one embodiment, the target polypeptide is a polypeptide containing a number of repeated amino acids directly correlated to the number of trinucleotide repeats transcribed/translated from DNA; from its mass alone the number of repeated trinucleotide repeats in the original DNA which coded it, may be deduced.

U.S. Pat. No. 6,020,208 utilizes a general category of probe elements (i.e., sample presenting means) with Surfaces Enhanced for Laser Desorption/Ionization (SELDI), within which there are three (3) separate subcategories. The SELDI process is directed toward a sample presenting means (i.e., probe element surface) with surface-associated (or surface-bound) molecules to promote the attachment (tethering or anchoring) and subsequent detachment of tethered analyte molecules in a light-dependent manner, wherein the said surface molecule(s) are selected from the group consisting of photoactive (photolabile) molecules that participate in the binding (docking, tethering, or crosslinking) of the analyte molecules to the sample presenting means (by covalent attachment mechanisms or otherwise).

PCT/EP97/04396 (WO 98/07036) teaches a process for determining the status of an organism by peptide measurement.

The reference teaches the measurement of peptides in a sample of the organism which contains both high and low molecular weight peptides and acts as an indicator of the organism's status. The reference concentrates on the measurement of low molecular weight peptides, i.e. below 30,000 Daltons, whose distribution serves as a representative cross-section of defined controls. Contrary to the methodology of the instant invention, the '396 patent strives to determine the status of a healthy organism, i.e. a "normal" and then use this as a reference to differentiate disease states. The present inventors do not attempt to develop a reference "normal", but rather strive to specify particular markers whose presence, absence or relative strength/concentration in disease vs. normal is diagnostic of at least one specific disease state or whose up-regulation or down-regulation is predictive of at least one specific disease state, whereby the presence of said marker serves as a positive indicator useful in distinguishing disease state. This leads to a simple method of analysis which can easily be performed by an untrained individual, since there is a positive correlation of data. On the contrary, the '396 patent requires a complicated analysis by a highly trained individual to determine disease state versus the perception of non-disease or normal physiology.

Richter et al, Journal of Chromatography B, 726 (1999) 25–35, refer to a database established from human hemofiltrate comprised of a mass database and a sequence database. The goal of Richter et al was to analyze the composition of the peptide fraction in human blood. Using MALDI-TOF, over 20,000 molecular masses were detected representing an estimated 5,000 different peptides. The conclusion of the study was that the hemofiltrate (HF) represented the peptide composition of plasma. No correlation of peptides with relation to normal and/or disease states is made.

As used herein, "analyte" refers to any atom and/or molecule; including their complexes and fragment ions. The term may refer to a single component or a set of components. In the case of biological molecules/macromolecules or "biopolymers", such analytes include but are not limited to: polypeptides, polynucleotides, proteins, peptides, antibodies, DNA, RNA, carbohydrates, steroids, and lipids, and any detectable moiety thereof, e.g. immunologically detectable fragments. Note that most important biomolecules under investigation for their involvement in the structure or regulation of life processes are quite large (typically several thousand times larger than $H_2O$).

As used herein, the term "molecular ions" refers to molecules in the charged or ionized state, typically by the addition or loss of one or more protons ($H^+$).

As used herein, the term "molecular fragmentation" or "fragment ions" refers to breakdown products of analyte molecules caused, for example, during laser-induced desorption (especially in the absence of added matrix).

As used herein, the term "solid phase" refers to the condition of being in the solid state, for example, on the probe element surface.

As used herein, "gas" or "vapor phase" refers to molecules in the gaseous state (i.e., in vacuo for mass spectrometry).

As used herein, the term "analyte desorption/ionization" refers to the transition of analytes from the solid phase to the gas phase as ions. Note that the successful desorption/ionization of large, intact molecular ions by laser desorption is relatively recent (circa 1988)—the big breakthrough was the chance discovery of an appropriate matrix (nicotinic acid).

As used herein, the term "gas phase molecular ions" refers to those ions that enter into the gas phase. Note that large molecular mass ions such as proteins (typical mass=60,000 to 70,000 times the mass of a single proton) are typically not volatile (i.e., they do not normally enter into the gas or vapor phase). However, in the procedure of the present invention, large molecular mass ions such as proteins do enter the gas or vapor phase.

As used herein in the case of MALDI, the term "matrix" refers to any one of several small, acidic, light absorbing chemicals (e.g., CHCA (alpha-cyano-4-hydroxy-cinnamic acid), nicotinic or sinapinic acid) that is mixed in solution with the analyte in such a manner so that, upon drying on the probe element, the crystalline matrix-embedded analyte molecules are successfully desorbed (by laser irradiation) and ionized from the solid phase (crystals) into the gaseous or vapor phase and accelerated as intact molecular ions. For the MALDI process to be successful, analyte is mixed with a freshly prepared solution of the chemical matrix (e.g., 10,000:1 matrix:analyte) and placed on the inert probe element surface to air dry just before the mass spectrometric analysis. The large fold molar excess of matrix, present at concentrations near saturation, facilitates crystal formation and entrapment of analyte.

As used herein, "energy absorbing molecules (EAM)" refers to any one of several small, light absorbing chemicals that, when presented on the surface of a probe, facilitate the neat desorption of molecules from the solid phase (i.e., surface) into the gaseous or vapor phase for subsequent acceleration as intact molecular ions. The term EAM is preferred, especially in reference to SELDI. Note that analyte desorption by the SELDI process is defined as a surface-dependent process (i.e., neat analyte may be placed on a surface composed of bound EAM or EAM and analyte may be mixed prior to placement on a surface). In contrast, MALDI is presently thought to facilitate analyte desorption by a volcanic eruption-type process that "throws" the entire surface into the gas phase. Furthermore, note that some EAM when used as free chemicals to embed analyte molecules as described for the MALDI process will not work (i.e., they do not promote molecular desorption, thus they are not suitable matrix molecules).

As used herein, "probe element" or "sample presenting device" refers to an element having the following properties: it is inert (for example, typically stainless steel) and active (probe elements with surfaces enhanced to contain EAM and/or molecular capture devices).

As used herein, "MALDI" refers to Matrix-Assisted Laser Desorption/Ionization.

As used herein, "TOF" stands for Time-of-Flight.

As used herein, "MS" refers to Mass Spectrometry.

As used herein, "MS/MS" refers to multiple sequential mass spectrometry.

As used herein "MALDI-TOF MS" refers to Matrix-assisted laser desorption/ionization time-of-flight mass spectrometry.

As used herein, "ESI" is an abbreviation for electrospray ionization.

As used herein, "chemical bonds" is used simply as an attempt to distinguish a rational, deliberate, and knowledgeable manipulation of known classes of chemical interactions from the poorly defined kind of general adherence observed when one chemical substance (e.g., matrix) is placed on another substance (e.g., an inert probe element surface). Types of defined chemical bonds include electrostatic or ionic (+/−) bonds (e.g., between a positively and negatively charged groups on a protein surface), covalent bonds (very strong or "permanent" bonds resulting from true electron sharing), coordinate covalent bonds (e.g., between electron donor groups in proteins and transition metal ions such as copper or iron), and hydrophobic interactions (such as between two noncharged groups), weak dipole and London force or induced dipole interactions.

As used herein, "electron donor groups" refers to the case of biochemistry, where atoms in biomolecules (e.g, N, S, O) "donate" or share electrons with electron poor groups (e.g., Cu ions and other transition metal ions).

As used herein, the term "biopolymer markers indicative or predictive of a disease state" is interpreted to mean that a biopolymer marker which is strongly present in a normal individual, but is down-regulated in disease is predictive of said disease; while alternatively, a biopolymer marker which is strongly present in a disease state, but is down-regulated in normal individuals, is indicative of said disease state. Biopolymer markers which are present in both disease and normal states are indicative/predictive based upon their relative strengths in disease vs. normal, along with the observation regarding when their signal strengthens/weakens relative to disease manifestation or progression.

As used herein, the term "disease state assessment" is interpreted to mean quantitative or qualitative determination of the presence/absence of the disease, with or without an ability to determine severity, rapidity of onset, or resolution of the disease state, e.g. a return to a normal physiological state.

As used herein, the term "therapeutic target recognition, development, and validation" refers to any concept or method which enables an artisan to recognize, develop, or validate the efficacy of a therapeutic moiety which is effected in conjunction with a chemical or physical interaction with one or more of the biopolymer markers of the instant invention.

As used herein, the term "polypeptide" is interpreted to mean a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. "Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well-known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

As used herein, the term "polynucleotide" is interpreted to mean a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces T.

As used herein, the term "detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P. D. Fahrlander and A. Klausner, Bio/Technology (1988) 6:1165.) Quantitation of the signal is achieved by, e.g., scintillation counting, densitometry, or flow cytometry.

As used herein, the term "antibody or antibodies" includes polyclonal and monoclonal antibodies of any isotype (IgA, IgG, IgE, IgD, IgM), or an antigen-binding portion thereof, including but not limited to F(ab) and Fv fragments, single chain antibodies, chimeric antibodies, humanized antibodies, and a Fab expression library. "Antibody" refers to a polypeptide ligand substantially encoded by an immunoglobulin gene or immunoglobulin genes, or fragments thereof, which specifically binds and recognizes an epitope (e.g., an antigen). The recognized immunoglobulin—genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies and humanized antibodies. "Fc" portion of an antibody refers to that portion of an immunoglobulin heavy chain that comprises one or more heavy chain constant region domains, $CH$, $CH_2$ and $CH_3$, but does not include the heavy chain variable region.

As used herein, the term "moieties" refers to an indefinite portion of a sample.

A "ligand" is a compound that specifically binds to a target molecule.

A "receptor" is a compound or portion of a structure that specifically binds to a ligand.

A ligand or a receptor (e.g., an antibody) "specifically binds to" or "is specifically immunoreactive with" a compound analyte when the ligand or receptor functions in a binding reaction which is determinative of the presence of the analyte in a sample of heterogeneous compounds. Thus, under designated assay (e.g., immunoassay) conditions, the ligand or receptor binds preferentially to a particular analyte and does not bind in a significant amount to other compounds present in the sample. For example, a polynucleotide specifically binds under hybridization conditions to an analyte polynucleotide comprising a complementary sequence; an antibody specifically binds under immunoassay conditions to an antigen analyte bearing an epitope against which the antibody was raised; and an adsorbent specifically binds to an analyte under proper elution conditions.

As used herein, the term "pharmaceutically effective carrier" refers to any solid or liquid material which may be used in creating formulations that further include active ingredients of the instant invention, e.g. biopolymer markers or therapeutics, for administration to a patient.

As used herein, the term "agent" is interpreted to mean a chemical compound, a mixture of chemical compounds, a sample of undetermined composition, a combinatorial small molecule array, a biological macromolecule, a bacteriophage peptide display library, a bacteriophage antibody (e.g., scFv) display library, a polysome peptide display library, or an extract made from biological materials such as bacteria, plants, fungi, or animal cells or tissues. Suitable techniques involve selection of libraries of recombinant antibodies in phage or similar vectors. See, Huse et al. (1989) Science 246: 1275–1281; and Ward et al. (1989) Nature 341: 544–546. The protocol described by Huse is rendered more efficient in combination with phage display technology. See, e.g., Dower et al., WO 91/17271 and McCafferty et al., WO 92/01047.

As used herein, the term "isolated" is interpreted to mean altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

As used herein, the term "variant" is interpreted to mean a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

As used herein, the term "biopolymer marker" refers to a polymer of biological origin, e.g. polypeptides, polynucleotides, polysaccharides or polyglycerides (e.g., di- or triglycerides), and may include any fragment, e.g. immunologically reactive fragments, variants or moieties thereof.

As used herein, the term "fragment" refers to the products of the chemical, enzymatic, or physical breakdown of an analyte. Fragments may be in a neutral or ionic state.

As used herein, the term "therapeutic avenues" is interpreted to mean any agents, modalities, synthesized compounds, etc., which interact with a biopolymer marker in any manner that facilitates a therapeutic benefit, including immunotherapeutic intervention, e.g. modalities such as administration of an immunologically reactive moiety capable of altering the course, progression and/or manifestation of the disease, as a result of interfering with the disease manifestation process, for example, at the early stages focused upon by the identification of the disease, such as by supplying a moiety capable of modifying the pathogenicity of lymphocytes specific for the biopolymer marker or related components.

As used herein, the term "interacting with a biopolymer marker" includes any process by which a biopolymer marker may physically or chemically relate with an organism, particularly when this interaction results in the development of therapeutic avenues or in modulation of the disease state.

As used herein, the term "therapeutic targets" may thus be defined as those analytes which are capable of exerting a modulating force, wherein "modulation" is defined as an alteration in function inclusive of activity, synthesis, production, and circulating levels. Thus, modulation effects the level or physiological activity of at least one particular disease related biopolymer marker or any compound or biomolecule whose presence, level or activity is linked either directly or indirectly, to an alteration of the presence, level, activity or generic function of the biopolymer marker, and may include pharmaceutical agents, biomolecules that bind to the biopolymer markers, or biomolecules or complexes to which the biopolymer markers bind. The binding of the biopolymer markers and the therapeutic moiety may result in activation (agonist), inhibition (antagonist), or an increase or decrease in activity or production (modulator) of the biopolymer markers or the bound moiety. Examples of such therapeutic moieties include, but are not limited to, antibodies, oligonucleotides, proteins (e.g., receptors), RNA, DNA, enzymes, peptides or small molecules. With regard to immunotherapeutic moieties, such a moiety may be defined as an effective analog for a major epitope peptide which has the ability to reduce the pathogenicity of key lymphocytes which are specific for the native epitope. An analog is defined as having structural similarity but not identity in peptide sequencing able to be recognized by T-cells spontaneously arising and targeting the endogenous self epitope. A critical function of this analog is an altered T-cell activation which leads to T-cell anergy or death.

With the advent of mass spectrometric methods such as MALDI and SELDI and ESI, researchers have begun to utilize a tool that holds the promise of uncovering countless biopolymers which result from translation, transcription and post-translational transcription of proteins from the entire genome.

Operating upon the principles of retentate chromatography, SELDI MS involves the adsorption of proteins, based upon their physico-chemical properties at a given pH and salt concentration, followed by selectively desorbing proteins from the surface by varying pH, salt, or organic solvent concentration. After selective desorption, the proteins retained on the SELDI surface, the "chip", can be analyzed using the CIPHERGEN protein detection system, or an equivalent thereof. Retentate chromatography is limited, however, by the fact that if unfractionated body fluids, e.g. blood, blood products, urine, saliva, cerebrospinal fluid, lymph and the like, along with tissue samples, are applied to the adsorbent surfaces, the biopolymers present in the greatest abundance will compete for all the available binding sites and thereby prevent or preclude less abundant biopolymers from interacting with them, thereby reducing or eliminating the diversity of biopolymers which are readily ascertainable.

If a process could be devised for maximizing the diversity of biopolymers discernable from a sample, the ability of researchers to accurately determine the relevance of such biopolymers with relation to one or more disease states would be immeasurably enhanced.

SUMMARY OF THE INVENTION

The instant invention is characterized by the use of a combination of preparatory steps, e.g. chromatography and 1-D tricine polyacrylamide gel electrophoresis. Subsequent to which the gel is stained, e.g. with Coomasie blue, silver or rubidium. Next, bands are selected from the gels for further study. Tryptic digestion of each band follows, concluding with the extraction of tryptic peptides from the digest. This extraction may be accomplished utilizing C18 ZIPTIPs, or organic extract and dry technique followed by MALDI Qq TOF (Maldi Quadrupole Quadrupole Time of Flight) processing.

Additional methodologies may include SELDI MS, 2-D gel technology, MALDI MS/MS and time-of-flight detection procedures to maximize the diversity of biopolymers which are verifiable within a particular sample. The cohort of biopolymers verified within a sample is then compared to develop data indicating their presence, absence or relative strength/concentration in disease vs normal controls, and further studied to determine whether the up-regulation or down-regulation of a single biopolymer or group of biopolymers is indicative of a disease state or predictive of the development of said disease state. Additionally, biopolymers recognized as being indicative or predictive of a disease state in accordance with the instant invention are useful in therapeutic intervention, e.g. as therapeutic modalities in their own right, in the course of therapeutic target recognition, in the development and validation of efficacious therapeutic modalities, e.g when interrogating or developing phage display libraries, and as ligands or receptors for use in conjunction with therapeutic intervention.

Although all manner of biomarkers related to all disease conditions are deemed to be within the purview of the instant invention and methodology, particular significance was given to those markers and diseases associated with the complement system, cognitive diseases, e.g. Alzheimer's disease and Syndrome X and diseases related thereto.

The complement system is an important part of non-clonal or innate immunity that collaborates with acquired immunity to destroy invading pathogens and to facilitate the clearance of immune complexes from the system. This system is the major effector of the humoral branch of the immune system, consisting of nearly 30 serum and membrane proteins. The proteins and glycoproteins composing the complement system are synthesized largely by liver hepatocytes. Activation of the complement system involves a sequential enzyme cascade in which the proenzyme product of one step becomes the enzyme catalyst of the next step. Complement activation can occur via two pathways: the classical and the alternative. The classical pathway is commonly initiated by the formation of soluble antigen-antibody complexes or by the binding of antibody to antigen on a suitable target, such as a bacterial cell. The alternative pathway is generally initiated by various cell-surface constituents that are foreign to the host. Each complement component is designated by numerals (C1–C9), by letter symbols, or by trivial names. After a component is activated, the peptide fragments are denoted by small letters. The complement fragments interact with one another to form functional complexes. Ultimately, foreign cells are destroyed through the process of a membrane-attack complex mediated lysis.

The C4 component of the complement system is involved in the classical activation pathway. It is a glycoprotein containing three polypeptide chains ($\alpha$, $\beta$, and $\gamma$). C4 is a substrate of component C1s and is activated when C1s hydrolyzes a small fragment (C4a) from the amino terminus of the $\alpha$ chain, exposing a binding site on the larger fragment (C4b).

The native C3 component consists of two polypeptide chains, $\alpha$ and $\beta$. As a serum protein, C3 is involved in the alternative pathway. Serum C3, which contains an unstable thioester bond, is subject to slow spontaneous hydrolysis into C3a and C3b. The C3f component is involved in the regulation required of the complement system which confines the reaction to designated targets. During the regulation process, C3b is cleaved into two parts: C3bi and C3f. C3bi is a membrane-bound intermediate wherein C3f is a free diffusible (soluble) component.

Complement components have been implicated in the pathogenesis of several disease conditions. C3 deficiencies have the most severe clinical manifestations, such as recurrent bacterial infections and immune-complex diseases, reflecting the central role of C3. The rapid profusion of C3f moieties and resultant "accidental" lysis of normal cells mediated thereby gives rise to a host of auto-immune reactions. The ability to understand and control these mechanisms, along with their attendant consequences, will enable practitioners to develop both diagnostic and therapeutic avenues by which to thwart these maladies.

In the course of defining a plurality of disease specific marker sequences, special significance was given to markers which were evidentiary of a particular disease state or with conditions associated with Syndrome-X. Syndrome-X is a multifaceted syndrome, which occurs frequently in the general population. A large segment of the adult population of industrialized countries develops this metabolic syndrome, produced by genetic, hormonal and lifestyle factors such as obesity, physical inactivity and certain nutrient excesses. This disease is characterized by the clustering of insulin resistance and hyperinsulinemia, and is often associated with dyslipidemia (atherogenic plasma lipid profile), essential hypertension, abdominal (visceral) obesity, glucose intolerance or noninsulin-dependent diabetes mellitus and an increased risk of cardiovascular events. Abnormalities of blood coagulation (higher plasminogen activator inhibitor type I and fibrinogen levels), hyperuricemia and microalbuminuria have also been found in metabolic syndrome-X.

The instant inventors view the Syndrome X continuum in its cardiovascular light, while acknowledging its important metabolic component. The first stage of Syndrome X consists of insulin resistance, abnormal blood lipids (cholesterol, triglycerides and free fatty acids), obesity, and high blood pressure (hypertension). Any one of these four first stage conditions signals the start of Syndrome X.

Each first stage Syndrome X condition risks leading to another. For example, increased insulin production is associated with high blood fat levels, high blood pressure, and obesity. Furthermore, the effects of the first stage conditions are additive; an increase in the number of conditions causes an increase in the risk of developing more serious diseases on the Syndrome X continuum.

A patient who begins the Syndrome X continuum risks spiraling into a maze of increasingly deadly diseases. The next stages of the Syndrome X continuum lead to overt diabetes, kidney failure, and heart failure, with the possibility of stroke and heart attack at any time. Syndrome X is a dangerous continuum, and preventative medicine is the best defense. Diseases are currently most easily diagnosed in their later stages, but controlling them at a late stage is extremely difficult. Disease prevention is much more effective at an earlier stage.

In a further contemplated embodiment of the invention, samples may be taken from a patient at one point in time, as a single sample or as multiple samples, or at different points in time such that analysis is carried out on multiple samples for ongoing analysis. Typically, a first sample is taken from a patient upon presentation with possible symptoms of a disease and analyzed according to the invention. Subsequently, some period of time after presentation, for example, about 3–6 months after the first presentation, a second sample is taken and analyzed according to the invention. The data can be used, by way of example, to diagnose or monitor a disease state, determine risk assessment, identify therapeutic avenues, or determine the therapeutic value of an agent such as a pharmaceutical.

Subsequent to the isolation of particular disease state marker sequences as taught by the instant invention, the promulgation of various forms of risk assessment tests are contemplated which will allow physicians to identify asymptomatic patients before they suffer an irreversible event such as diabetes, kidney failure, and heart failure, and enable effective disease management and preventative medicine. Additionally, the specific diagnostic tests which evolve from this methodology provide a tool for rapidly and accurately diagnosing acute Syndrome X events such as heart attack and stroke, and facilitate treatment.

More particularly, biopolymer markers elucidated via methodologies of the instant invention find utility related to broad areas of disease therapeutics. Such therapeutic avenues include, but are not limited to:

1) utilization and recognition of said biopolymer markers, variants or moieties thereof as direct therapeutic modalities, either alone or in conjunction with an effective amount of a pharmaceutically effective carrier;

2) validation of therapeutic modalities or disease preventative agents as a function of biopolymer marker presence or concentration;

3) treatment or prevention of a disease state by formation of disease intervention modalities; e.g. formation of biopolymer/ligand conjugates which intervene at receptor sites to prevent, delay or reverse a disease process;

4) use of biopolymer markers or moieties thereof as a means of elucidating therapeutically viable agents, e.g. from a bacteriophage peptide display library, a bacteriophage antibody library or the like;

5) instigation of a therapeutic immunological response; and 6) synthesis of molecular structures related to said biopolymer markers, moieties or variants thereof which are constructed and arranged to therapeutically intervene in the disease process.

A process for identifying or developing therapeutic avenues related to a disease state utilizing any of the above examples may follow results obtained from conducting an analysis inclusive of interacting with a biopolymer including the sequence of the particular disease specific marker or at least one analyte thereof of the present invention. Such treatment or prevention of a disease state by formation of disease intervention modalities may be by the formation of biopolymer/ligand conjugates which intervene at receptor sites to prevent, delay, or reverse a disease process. In addition, a means of elucidating therapeutically viable agents may include the use of a bacteriophage peptide display library or a bacteriophage antibody library. The therapeutic avenues may regulate the presence or absence of the biopolymer including the sequence of the particular disease specific marker or at least one analyte thereof in the present invention.

Accordingly, it is an objective of the instant invention to define a disease specific biopolymer marker sequence which is useful in evidencing and categorizing at least one particular disease state.

It is an additional objective of the instant invention to develop methods and means of disease therapy, including but not limited to:

1) utilization and recognition of said biopolymer markers, variants or moieties thereof as direct therapeutic modalities, either alone or in conjunction with an effective amount of a pharmaceutically effective carrier;

2) validation of therapeutic modalities or disease preventative agents as a function of biopolymer marker presence or concentration;

3) treatment or prevention of a disease state by formation of disease intervention modalities; e.g. formation of biopolymer/ligand conjugates which intervene at receptor sites to prevent, delay or reverse a disease process;

4) use of biopolymer markers or moieties thereof as a means of elucidating therapeutically viable agents, e.g. from a bacteriophage peptide display library, a bacteriophage antibody library or the like;

5) instigation of a therapeutic immunological response; and 6) synthesis of molecular structures related to said biopolymer markers, moieties or variants thereof which are constructed and arranged to therapeutically intervene in the disease process, e.g. by directly determining the three-dimensional structure of said biopolymer marker directly from an amino acid sequence thereof.

It is another objective of the instant invention to evaluate samples containing a plurality of biopolymers for the presence of disease specific biopolymer marker sequences (disease specific markers) which evidence a link to at least one specific disease state.

It is a further objective of the instant invention to elucidate essentially all biopolymeric markers, moieties or variants thereof contained within said samples, whereby particularly significant moieties may be identified.

It is a further objective of the instant invention provide at least one purified antibody which is specific to said disease specific marker sequence.

It is yet another objective of the instant invention to teach a monoclonal antibody which is specific to said disease specific marker sequence.

It is a still further objective of the invention to teach polyclonal antibodies raised against said disease specific marker.

It is yet an additional objective of the instant invention to teach a diagnostic kit for determining the presence, concentration, or relative strength/concentration of said disease specific marker.

It is a still further objective of the instant invention to teach methods for characterizing disease state based upon the identification of said disease specific marker.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
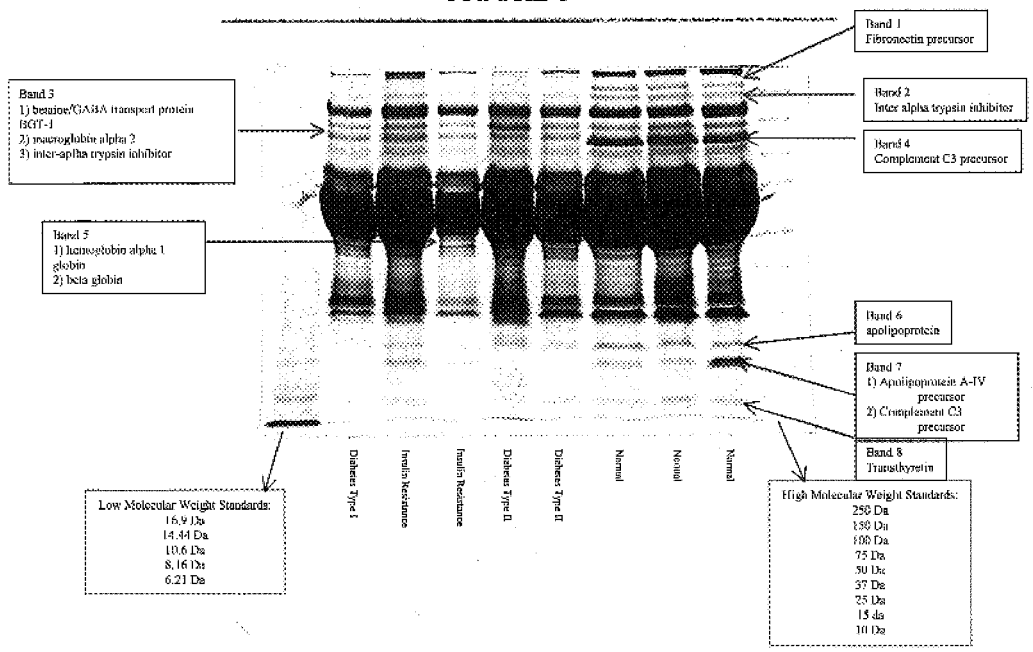
FIG. 1 is a photograph of a tricine gel HiQ 1 (Elution) comparing Insulin Resistance versus Normal.
Figure 2:
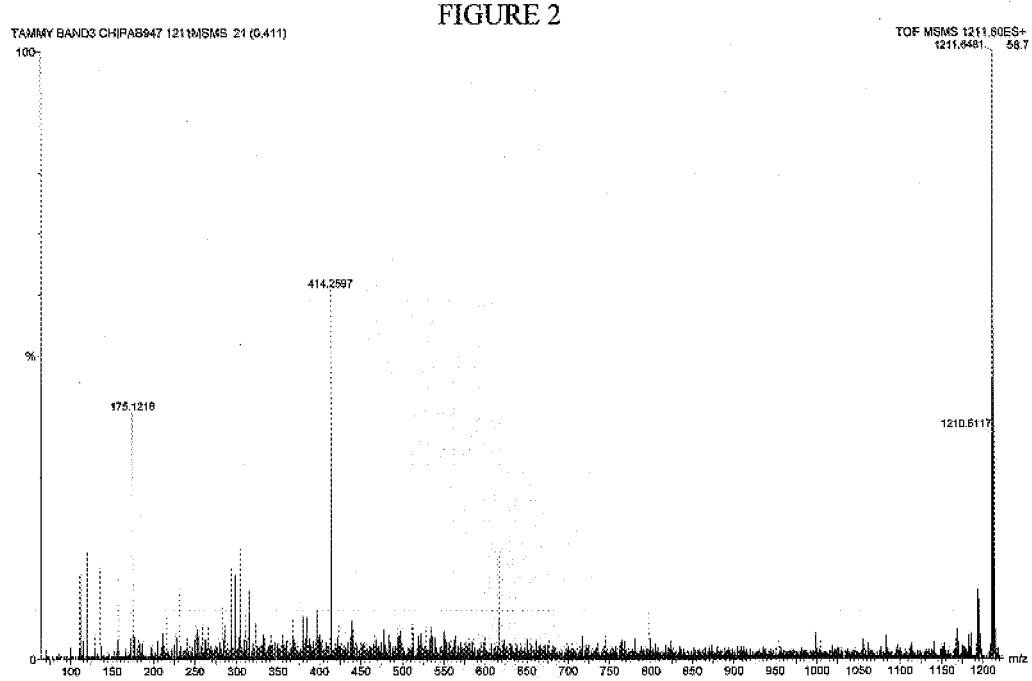
FIG. 2 is a trypsin digested spectra graph depicting the characteristic profile of the ion 1211 (SEQ ID NO:2)
Figure 3:
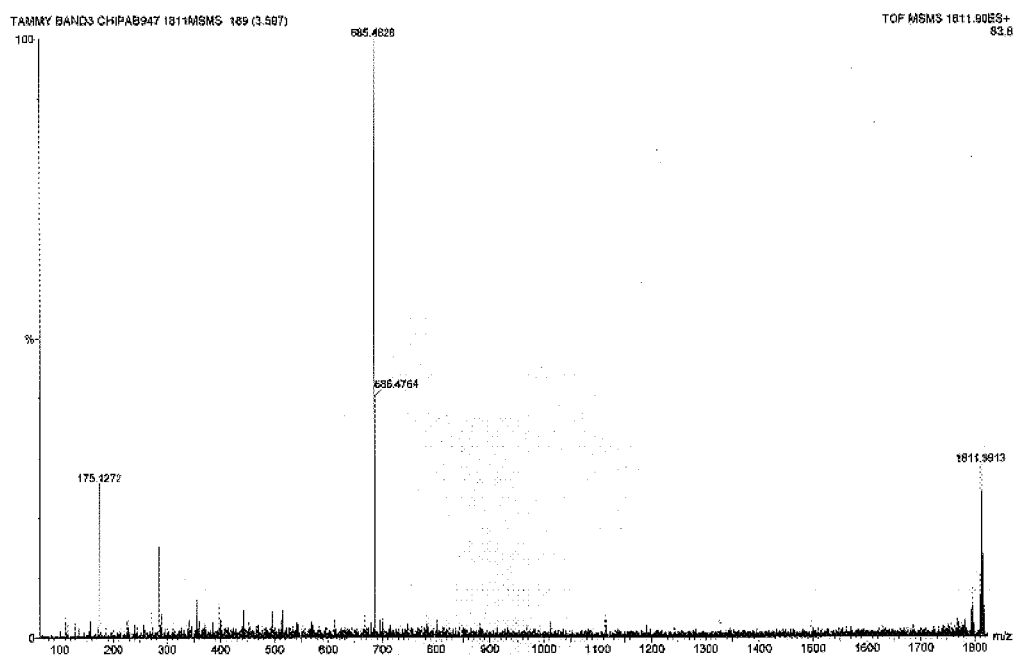
FIG. 3 is a trypsin digested spectra graph depicting the characteristic profile of the ion 1811 (SEQ ID NO:1).

In earlier work, for example in U.S. patent application Ser. No. 09/846330 filed Apr. 30, 2000, the contents of which is herein incorporated by reference, raw sera was obtained and mixed with formic acid and extracted the peptides with C18 reversed phase ZIPTIPs.

In the instantly disclosed invention, we deal with proteins generally having a molecular weight of about 20 kD or more. In general, proteins of greater than 20 kD can reliably be fragmented by trypsin or other enzymes. The instant technology incorporates sufficient sensitivity to deal with even the low production of peptides from proteins less than 20 kD clipped from gel.

Proteins differ from peptides in that they cannot be effectively resolved by time of flight MS and they are too large (>3 kD) to be effectively fragmented by collision with gases. The most commonly used solution to these problems is to resolve the proteins by polyacrylamide gel electrophoresis followed by staining with silver, or coomasie brilliant blue or rubidium dyes or counter staining with Zinc-SDS complexes. Once the proteins have been resolved and visualized with stains the proteins that differ between disease states can then be excised from the gel and the protein purified in the 1-D gel band or 2-D gel spot can be cleaved into fragments less that 3 kD by proteolytic enzymes. Once protein has been resolved by gel and cleaved by enzymes, the protein is considered in the form of peptides and therefore can be dealt with as per earlier work (09/846330). The peptide is either collected and purified with C18 reversed phase chromatography or by some other form of chromatography prior to reversed phase separation. The peptide can also be collected in ammonium carbonate buffer that is subsequently evolved by reaction with acid or by removal in organic solvents.

Once the peptides are collected they can be sequenced, e.g. with a MALDI-Qq-TOF but also with a TOF-TOF, and ESI-Q-TOF or an ION-TRAP. Other types of MS analysis which may be employed are SELDI MS and MS/MS. The peptides are fragments of the original protein. The peptides are sequenced by fragmentation to produced a spectrum composed of the parts of the peptide. The peptide fragments can be produced by a strong ionization energy with a laser, temperature, electron capture, collision between the peptides themselves or with other objects such as gas molecules. The spacing in terms of mass between the parts of the peptides is a fragmentation pattern. The fragmentation pattern of each peptide from the starting mass to the last remaining amino acid (from either end) is unique.

The human genome contains the genes that encode all proteins. The proteolytic cut sites within all these proteins can be predicted from the translated amino acid sequence. The mass of the peptides that result from the predicting cut sites can be calculated. Similarly, the fragmentation pattern from each hypothetical peptide can be predicted. Thus, we can conceptually digest the proteins within the human proteome and fragment them.

When a peptide has been "sequenced" it is understood that the peptide fragment has been purified by one of the methods above, i.e. Time of flight (TOF) or by chromatography, before fragmenting it with gas to produce the peptide fragments. The original peptide mass and fragmentation pattern obtained is then fit to those from the theoretical digestion and fragmentation of the genome. The peptide that best matches the theoretical peptides and fragments and is biologically possible, i.e. a potential human blood-borne protein, is thus identified. It is possible to identify plural targets in this fashion.

Following are exemplary, but non-limiting examples of preparatory protocols useful in the process of the instant invention.

Preparatory Protocols:

Any of these protocols may be selected from a column flow-through stream, a column elution stream, or a column scrub stream.

Hi Q is a strong anion exchanger made of methyl acrylate co-polymer with the functional group: —N$^+$ (CH$_3$)$_2$;

Hi S is a strong cation exchanger made of methyl acrylate co-polymer with the functional group: —SO$_3^-$;

DEAE is a diethylaminoethyl which is a weak cation exchanger made of methyl acrylate co-polymer with the functional group: —N$^+$ (C$_2$H$_5$)$_2$, PS is phenyl SEPHAROSE;

BS is buytl SEPHAROSE.

Note that the supports, i.e. methyl acrylate and SEPHAROSE are different, but non-limiting examples, as the same functional group on different supports will function, albeit possibly with different effects.

DEAE Column Protocol:
1) Cast 200 µl of 50% slurry;
2) Equilibrate column in 5 bed volumes of 50 mM tricine pH 8.8 (binding buffer);
3) Dissolve 25 µl of sera in 475 µl of binding buffer;
4) Wash column in 5 bed volumes of binding buffer;
5) Elute column in 120 µl of 0.4 M Phosphate buffer (PB) pH 6.1;
6) Elute column in 120 µl of 50 mM citrate buffer pH 4.2;
7) Scrub column with 120 µl sequentially with each of 0.1% TRITON, 1.0% TRITON and 2% SDS in 62.5 mM TRIS pH 6.8.

Butyl SEPHAROSE Column Protocol:
1) Cast 150 µl bed volume column;
2) Equilibrate column in 5 bed volumes of 1.7 M $(NH_4)_2SO_4$ in 50 mM PB pH 7.0 (binding buffer);
3) Dissolve 35 µl of sera in 465 µl of binding buffer and apply;
4) Wash column in 5 bed volumes of binding buffer;
5) Elute column in 120 µl of 0.4 M $(NH_4)_2SO_4$ in 50 mM PB pH 7.0;
6) Elute column in 120 µl of 50 mM PB pH 7.0;
7) Scrub column with 120 µl sequentially with each of 0.1% TRITON, 1.0% TRITON and 2% SDS in 62.5 mM TRIS pH 6.8.

Phenyl SEPHAROSE Column Protocol:
1) Cast 150 µl bed volume column;
2) Equilibrate column in 5 bed volumes of 1.7 M $(NH_4)_2SO_4$ in 50 mM PB pH 7.0 (binding buffer);
3) Dissolve 35 µl of sera in 465 µl of binding buffer and apply;
4) Wash column in 5 bed volumes of binding buffer;
5) Elute column in 120 µl of 0.2 M $(NH_4)_2SO_4$ in 50 mM PB pH 7.0;
6) Elute column in 120 µl of 50 mM PB pH 7.0;
7) Scrub column with 120 µl sequentially with each of 0.1% TRITON, 1.0% TRITON and 2% SDS in 62.5 mM TRIS pH 6.8.

HiQ Anion Exchange Mini Column Protocol:
1) Dilute sera in sample/running buffer;
2) Add HiQ resin to column and remove any air bubbles;
3) Add ultrafiltered (UF) water to aid in column packing;
4) Add sample/running buffer to equilibrate column;
5) Add diluted sera;
6) Collect all the flow-through fraction in EPPENDORF tubes until level is at resin;
7) Add sample/running buffer to wash column;
8) Add elution buffer and collect elution in EPPENDORF tubes.

HiS Cation Exchange Mini Column Protocol:
1) Dilute sera in sample/running buffer;
2) Add HiS resin to column and remove any air bubbles;
3) Add UF water to aid in column packing;
4) Add sample/running buffer to equilibrate column for sample loading;
5) Add diluted sera to column;
6) Collect all flow through fractions in EPPENDORF tubes until level is at resin;
7) Add sample/running buffer to wash column;
8) Add elution buffer and collect elution in EPPENDORF tubes.

Illustrative of the various buffering compositions useful in this technique are: Sample/Running buffers: including but not limited to Bicine buffers of various molarities, pH's, NaCl content, BIS-TRIS buffers of various molarities, pH's, NaCl content, Diethanolamine of various molarities, pH's, NaCl content, Diethylamine of various molarities, pH's, NaCl content, Imidazole of various molarities, pH's, NaCl content, Tricine of various molarities, pH's, NaCl content, Triethanolamine of various molarities, pH's, NaCl content, TRIS of various molarities, pH's, NaCl content. Elution Buffer: Acetic acid of various molarities, pH's, NaCl content, Citric acid of various molarities, pH's, NaCl content, HEPES of various molarities, pH's, NaCl content, MES of various molarities, pH's, NaCl content, MOPS of various molarities, pH's, NaCl content, PIPES of various molarities, pH's, NaCl content, Lactic acid of various molarities, pH's, NaCl content, Phosphate of various molarities, pH's, NaCl content, Tricine of various molarities, pH's, NaCl content.

Following tryptic digestion, additional processing may be carried out, for example:

Utilizing a type of micro-chromatographic column called a C18-ZIPTIP available from the Millipore company, the following preparatory steps were conducted.
1. Dilute sera in sample buffer
2. Aspirate and dispense ZIPTIP in 50% Acetonitrile
3. Aspirate and dispense ZIPTIP in Equilibration solution
4. Aspirate and dispense in serum sample
5. Aspirate and dispense ZIPTIP in Wash solution
6. Aspirate and dispense ZIPTIP in Elution Solution Illustrative of the various buffering compositions useful in the present invention are:
Sample Buffers (various low pH's): Hydrochloric acid (HCl), Formic acid, Trifluoroacetic acid (TFA),
Equilibration Buffers (various low pH's): HCl, Formic acid, TFA;
Wash Buffers (various low pH's): HCl, Formic acid, TFA;
Elution Solutions (various low pH's and % Solvents): HCl, Formic acid, TFA;
Solvents: Ethanol, Methanol, Acetonitrile. Spotting was then performed, for example upon a Gold Chip the following manner:
1. Spot 2 ul of sample onto each spot
2. Let sample partially dry As a result of these procedures, the disease specific markers Inter alpha trypsin Inhibitor having a molecular weight of about 1811.9503 daltons and a sequence of SEQ ID NO:1 and betaine/GABA transport protein having a molecular weight of about 1211.5591 daltons and a sequence of SEQ ID NO:2 related to Insulin Resistance were found.

FIG. 1 is a photograph of a gel which is indicative of the presence/absence of the marker in disease vs. control and, in cases where the marker is always present, the relative strength, e.g. the up or down regulation of the marker relative to categorization of disease state is deduced.

A method for evidencing and categorizing at least one disease state is disclosed. The steps taken include obtaining a sample from a patient, preferably human, and conducting MS analysis on the sample. As a result, at least one biopolymer marker sequence or analyte thereof is isolated from the sample which undergoes evidencing and categorizing and is compared to the biopolymer marker sequence as disclosed in the present invention. The step of evidencing and categorizing is particularly directed to biopolymer markers or analytes thereof linked to at least one risk of disease development of the patient or related to the existence of a particular disease state.

In addition, various kits are contemplated for use by the present invention. One such kit provides for determining the presence of the disease specific biopolymer marker. At least one biochemical material is incorporated which is capable of specifically binding with a biomolecule which includes at least the disease specific biopolymer marker or analyte thereof, and a means for determining binding between the biochemical material and the biomolecule. The biochemical material for any of the contemplated kits, by way of example an antibody or at least one monoclonal antibody specific therefore, or biomolecule may be immobilized on a solid support and include at least one labeled biochemical material which is preferably an antibody. The sample utilized for any of the kits may be a fractionated or unfractionated body fluid or a tissue sample. Non-limiting examples of such fluids are blood, blood products, urine, saliva, cerebrospinal fluid, and lymph.

Further contemplated is a kit for diagnosing, determining risk-assessment, and identifying therapeutic avenues related to a disease state. This kit includes at least one biochemical material which is capable of specifically binding with a biomolecule which includes at least one biopolymer marker including the sequence of the particular disease specific biopolymer marker or an analyte thereof related to the disease state. Also included is a means for determining binding between the biochemical material and the biomolecule, whereby at least one analysis to determine a presence of a marker, analyte thereof, or a biochemical material specific thereto, is carried out on a sample. As previously described, analysis may be carried out on a single sample or multiple samples.

In accordance with various stated objectives of the invention, the skilled artisan, in possession of the specific disease specific marker as instantly disclosed, would readily carry out known techniques in order to raise purified biochemical materials, e.g. monoclonal and/or polyclonal antibodies, which are useful in the production of methods and devices useful as point-of-care rapid assay diagnostic or risk assessment devices as are known in the art.

The specific disease markers which are analyzed according to the method of the invention are released into the circulation and may be present in the blood or in any blood product, for example plasma, serum, cytolyzed blood, e.g. by treatment with hypotonic buffer or detergents and dilutions and preparations thereof, and other body fluids, e.g. cerebrospinal fluid (CSF), saliva, urine, lymph, and the like. The presence of each marker is determined using antibodies specific for each of the markers and detecting specific binding of each antibody to its respective marker. Any suitable direct or indirect assay method may be used to determine the level of each of the specific markers measured according to the invention. The assays may be competitive assays, sandwich assays, and the label may be selected from the group of well-known labels such as radioimmunoassay, fluorescent or chemiluminescence immunoassay, or immunoPCR technology. Extensive discussion of the known immunoassay techniques is not required here since these are known to those of skill in the art. See Takahashi et al. (din Chem 1999; 45(8): 1307) for a detailed example of an assay.

A monoclonal antibody specific against the disease marker sequence isolated by the present invention may be produced, for example, by the polyethylene glycol (PEG) mediated cell fusion method, in a manner well-known in the art.

Traditionally, monoclonal antibodies have been made according to fundamental principles laid down by Kohler and Milstein. Mice are immunized with antigens, with or without, adjuvants. The splenocytes are harvested from the spleen for fusion with immortalized hybridoma partners. These are seeded into microtiter plates where they can secrete antibodies into the supernatant that is used for cell culture. To select from the hybridomas that have been plated for the ones that produce antibodies of interest, the hybridoma supernatants are usually tested for antibody binding to antigens in an ELISA (enzyme linked immunosorbent assay) assay. The idea is that the wells that contain the hybridoma of interest will contain antibodies that will bind most avidly to the test antigen, usually the immunizing antigen. These wells are then subcloned in limiting dilution fashion to produce monoclonal hybridomas. The selection for the clones of interest is repeated using an ELISA assay to test for antibody binding. Therefore, the principle that has been propagated is that in the production of monoclonal antibodies the hybridomas that produce the most avidly binding antibodies are the ones that are selected from among all the hybridomas that were initially produced. That is to say, the preferred antibody is the one with highest affinity for the antigen of interest.

There have been many modifications of this procedure such as using whole cells for immunization. In this method, instead of using purified antigens, entire cells are used for immunization. Another modification is the use of cellular ELISA for screening. In this method instead of using purified antigens as the target in the ELISA, fixed cells are used. In addition to ELISA tests, complement mediated cytotoxicity assays have also been used in the screening process. However, antibody-binding assays were used in conjunction with cytotoxicity tests. Thus, despite many modifications, the process of producing monoclonal antibodies relies on antibody binding to the test antigen as an endpoint.

The purified monoclonal antibody is utilized for immunochemical studies.

Polyclonal antibody production and purification utilizing one or more animal hosts in a manner well-known in the art can be performed by a skilled artisan.

Another objective of the present invention is to provide reagents for use in diagnostic assays for the detection of the particularly isolated disease specific marker sequences of the present invention.

In one mode of this embodiment, the marker sequences of the present invention may be used as antigens in immunoassays for the detection of those individuals suffering from the disease known to be evidenced by said marker sequence. Such assays may include but are not limited to: radioimmunoassay, enzyme-linked immunosorbent assay (ELISA), "sandwich" assays, precipitin reactions, gel diffusion immunodiffusion assay, agglutination assay, fluorescent immunoassays, protein A or G immunoassays and immunoelectrophoresis assays.

According to the present invention, monoclonal or polyclonal antibodies produced against the disease specific marker sequence of the instant invention are useful in an immunoassay on samples of blood or blood products such as serum, plasma or the like, cerebrospinal fluid or other body fluid, e.g. saliva, urine, lymph, and the like, to diagnose patients with the characteristic disease state linked to said marker sequence. The antibodies can be used in any type of immunoassay. This includes both the two-site sandwich assay and the single site immunoassay of the non-competitive type, as well as in traditional competitive binding assays.

Particularly preferred, for ease and simplicity of detection, and its quantitative nature, is the sandwich or double antibody assay of which a number of variations exist, all of which are contemplated by the present invention. For example, in a typical sandwich assay, unlabeled antibody is immobilized on a solid phase, e.g. microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen.

Antibodies may also be utilized against the disease specific markers, as haptens, to create an antibody response against the protein to which it binds, thereby identifying targets for treatment of the disease or a sub-class thereof.

Lastly, the markers and associated antibodies provide a tool for monitoring the progress of a patient during a therapeutic treatment, so as to determine the usefulness of a novel therapeutic agent.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures.

One skilled in the art will readily appreciate that the present invention is well adapted to carry out the objectives and obtain the ends and advantages mentioned, as well as those inherent therein. The oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An isolated biopolymer marker peptide consisting of SEQ ID NO: 2 diagnostic for insulin resistance.

2. A method for diagnosing insulin resistance comprising:
   (a) obtaining a sample from a patient;
   (b) conducting mass spectrometric analysis on said sample to elucidate peptide fragments contained therein; and
   (c) comparing mass spectrum profiles of an isolated biopolymer marker peptide consisting of SEQ ID NO:2 to mass spectrum profiles of peptides elucidated from said sample; wherein recognition of a mass spectrum profile in the sample displaying the characteristic profile of the mass spectrum profile for the isolated biopolymer marker peptide consisting of SEQ ID NO:2 having a molecular weight of about 1212 daltons is diagnostic for insulin resistance.

3. The method of claim 2, wherein said sample as an unfractionated body fluid or a tissue sample.

4. The method of claim 2, wherein said sample is selected from the group consisting of blood, blood products, urine, saliva, cerebrospinal fluid, and lymph.

5. The method of claim 2, wherein said mass spectrometric analysis is selected from the group consisting of Surface Enhanced Laser Desorption Ionization (SEIJDI) mass spectrometry (MS), Matrix-Assisted Laser Desorption/ Quadrupole quadrupole Time-Of-Flight (MALDI-TOF) mass spectrometry, multiple sequential Mass Spectrometry (MS/MS), multiple sequential Time-Of-Flight/Time-of-Flight (TOF-TOF) mass spectrometry, Electrospray Ionization/Ionization Time-Of-Flight (ESI-O-TOF) mass spectrometry and lON-TRAP mass spectrometry.

6. The method of claim 2, wherein said patient is a human.

7. An insulin resistance diagnostic kit comprising: (a) a biopolymer marker peptide consisting of SEQ ID NO: 2 and (b) an antibody that binds to said biopolymer marker pepbide in a sample from a patient.

8. The insulin resistance diagnostic kit of claim 7, wherein said antibody is immobilized on a solid support.

9. The insulin resistance diagnostic kit of claim 7, wherein said antibody is labeled.

* * * * *

SEQUENCE LISTING

<160> NUMBER OF SEQ ID NOS: 2

<210> SEQ ID NO 1
<211> LENGTH: 18
<212> TYPE: PRT
<213> ORGANISM: Homo sapiens

<400> SEQUENCE: 1

Lys Ser Pro Glu Gln Gln Glu Thr Val Leu Asp Gly Asn Leu Ile Ile
1               5                   10                  15

Arg Tyr

<210> SEQ ID NO 2
<211> LENGTH: 13
<212> TYPE: PRT
<213> ORGANISM: Homo sapiens

<400> SEQUENCE: 2

Lys Gln His Pro Cys Leu Asp Gly Ser Ala Gly Arg Asn
1               5                   10